US 12,372,388 B2

(12) United States Patent
Ito

(10) Patent No.: US 12,372,388 B2
(45) Date of Patent: Jul. 29, 2025

(54) FLUID ANALYSIS APPARATUS, FLUID ANALYSIS METHOD, AND FLUID ANALYSIS PROGRAM

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 759 days.

(21) Appl. No.: 17/735,085

(22) Filed: May 2, 2022

(65) Prior Publication Data

US 2022/0268612 A1     Aug. 25, 2022

Related U.S. Application Data

(63) Continuation of application No. PCT/JP2020/042072, filed on Nov. 11, 2020.

(30) Foreign Application Priority Data

Dec. 25, 2019    (JP) ................................ 2019-235139

(51) Int. Cl.
    *G01F 1/7086*     (2022.01)
    *G01R 33/563*     (2006.01)
    *G06V 20/69*     (2022.01)

(52) U.S. Cl.
    CPC ..... *G01F 1/7086* (2013.01); *G01R 33/56316* (2013.01); *G06V 20/693* (2022.01)

(58) Field of Classification Search
None
See application file for complete search history.

(56) References Cited

U.S. PATENT DOCUMENTS

| 2018/0146952 | A1 | 5/2018 | Du et al. |
| 2019/0365354 | A1 | 12/2019 | Du |
| 2021/0358125 | A1* | 11/2021 | Payeli ................ G06T 7/62 |

FOREIGN PATENT DOCUMENTS

| JP | H0833625 | 2/1996 |
| JP | 2006000421 | 1/2006 |
| JP | 2015073801 | 4/2015 |

OTHER PUBLICATIONS

"International Search Report (Form PCT/ISA/210) of PCT/JP2020/042072," mailed on Jan. 26, 2021, with English translation thereof, pp. 1-5.

"Written Opinion of the International Searching Authority (Form PCT/ISA/237)" of PCT/JP2020/042072, mailed on Jan. 26, 2021, with English translation thereof, pp. 1-6.

* cited by examiner

*Primary Examiner* — Haris Sabah
(74) *Attorney, Agent, or Firm* — JCIPRNET

(57) ABSTRACT

A processor analyzes an image obtained by imaging a subject including a tubular structure in which a fluid flows, thereby deriving fluid information regarding flow of the fluid at each of pixel positions in the tubular structure. The processor derives, within the tubular structure included in the image, a matching degree between the fluid information at a plurality of pixel-of-interest positions set at a first sampling interval and the fluid information at a plurality of pixel positions within a predetermined region based on the pixel-of-interest positions. The processor sets a second sampling interval for displaying the fluid information in accordance with the matching degree. The processor samples the fluid information at the set second sampling interval and causes a display to display the fluid information.

17 Claims, 14 Drawing Sheets

FIG. 5

| SIZE (mm) | FIRST SAMPLING INTERVAL (PIXELS) |
|---|---|
| 0 TO 10 | 2 |
| 10 TO 15 | 4 |
| 15 TO 20 | 6 |
| 20 TO 25 | 8 |
| 25 TO 30 | 10 |
| 30 TO 35 | 12 |

~LUT1

FLUID ANALYSIS APPARATUS, FLUID ANALYSIS METHOD, AND FLUID ANALYSIS PROGRAM

CROSS-REFERENCE TO RELATED APPLICATIONS

This application is a Continuation of PCT International Application No. PCT/JP2020/042072 filed on Nov. 11, 2020, which claims priority under 35 U.S.C § 119(a) to Japanese Patent Application No. 2019-235139 filed on Dec. 25, 2019. Each of the above application(s) is hereby expressly incorporated by reference, in its entirety, into the present application.

BACKGROUND OF THE INVENTION

1. Field of the Invention

The present disclosure relates to a fluid analysis apparatus, a fluid analysis method, and a fluid analysis program for analyzing and displaying flow of a fluid.

2. Description of the Related Art

In recent years, blood flow in blood vessels has been analyzed by using a medical image obtained by imaging a heart, a brain, or the like. As a blood flow analysis method using such a medical image, for example, a 4D flow method of measuring actual blood flow four-dimensionally has been used. In the 4D flow method, for example, by using a three-dimensional magnetic resonance imaging (MRI) image captured by three-dimensional cine phase contrast magnetic resonance imaging, a flow velocity vector is derived for each voxel, each pixel, or each region, and the flow velocity vectors are dynamically displayed along with the flow of time. A method for simulating blood flow by a blood flow analysis using computational fluid dynamics (CFD) has also been used.

In addition, a method has been proposed for displaying results of the above 4D flow and CFD analysis by, for example, streamlines, path lines, streak lines, or the like, to display the blood flow three-dimensionally.

To visualize the blood flow in a state close to the actual flow in blood vessels, a flow velocity vector may be displayed for each voxel of an MRI image. However, if the flow velocity vectors are drawn for all the voxels, the information amount becomes enormous, and drawing processing requires an enormous amount of time. In addition, if the flow velocity vectors are displayed for all the voxels, intervals between the flow velocity vectors become so dense that it is difficult to grasp the analysis results.

On the other hand, by increasing or decreasing sampling intervals for displaying the flow velocity vectors, the quantity of flow velocity vectors to be displayed can be increased or decreased. However, if the sampling intervals are fixed, it may be difficult to view the displayed flow velocity vectors because, for example, the flow velocity vectors may be drawn roughly in a portion to be focused on in blood vessels or, on the contrary, the flow velocity vectors may be drawn densely in a portion where not so much information is necessary.

Thus, various methods for setting the sampling intervals of the flow velocity vectors have been proposed. For example, JP1996-33625A (JP-H-8-33625A) proposes a method for setting the sampling intervals in accordance with a displayed body part, a display depth, the area of a region of interest, or the like, when displaying the flow velocity vectors on the basis of information on a blood flow velocity obtained from an ultrasound diagnostic apparatus. In addition, JP2006-000421A proposes a method for displaying the flow velocity vectors at an appropriate density by thinning out the flow velocity vectors when displaying the flow velocity vectors on the basis of information on a blood flow velocity obtained from an ultrasound diagnostic apparatus.

SUMMARY OF THE INVENTION

However, if the sampling intervals of the flow velocity vectors are set in accordance with the displayed body part or display depth as in the method described in JP1996-33625A (JP-H-8-33625A), the flow velocity vectors may be drawn roughly in a portion to be focused on in blood vessels or, on the contrary, the flow velocity vectors may be drawn densely in a portion where not so much information is necessary. In addition, by setting the sampling intervals in accordance with the area of a region of interest, a user needs to set the region of interest. Furthermore, although the flow velocity vectors are thinned out in the method described in JP2006-000421A, the reference for thinning out the flow velocity vectors is not clear.

The present disclosure has been made in view of the above circumstances, and an object thereof is to enable fluid information such as a flow velocity vector to be displayed at an appropriate sampling interval without imposing a load on a user.

A fluid analysis apparatus according to the present disclosure includes at least one processor configured to:

analyze an image obtained by imaging a subject including a tubular structure in which a fluid flows, thereby deriving fluid information regarding flow of the fluid at each of pixel positions in the tubular structure;

derive, within the tubular structure included in the image, a matching degree between the fluid information at a plurality of pixel-of-interest positions set at a first sampling interval and the fluid information at a plurality of pixel positions within a predetermined region based on the pixel-of-interest positions;

set a second sampling interval for displaying the fluid information in accordance with the matching degree; and sample the fluid information at the set second sampling interval and cause a display to display the fluid information.

Examples of "fluid information regarding flow of the fluid" include a flow velocity vector, a wall shear stress (WSS), a vorticity, and the like.

In the fluid analysis apparatus according to the present disclosure, the processor may be configured to set the first sampling interval in accordance with a size of a region intersecting a center line of the tubular structure included in the image.

In the fluid analysis apparatus according to the present disclosure, the processor may be configured to set the second sampling interval that is larger as the matching degree is larger.

In the fluid analysis apparatus according to the present disclosure, the processor may be configured to set the second sampling interval to the first sampling interval if the matching degree is greater than or equal to a predetermined threshold.

In the fluid analysis apparatus according to the present disclosure, the processor may be configured to cause the display to display representative fluid information that represents the fluid information within the region.

In the fluid analysis apparatus according to the present disclosure, the processor may be configured to set the second sampling interval in accordance with a size of a region intersecting a center line of the tubular structure included in the image if the matching degree is less than a predetermined threshold.

In the fluid analysis apparatus according to the present disclosure, the processor may be configured to set the second sampling interval in a direction intersecting the center line of the tubular structure.

In the fluid analysis apparatus according to the present disclosure, the processor may be configured to cause the display to display the fluid information as a vector.

In the fluid analysis apparatus according to the present disclosure, the processor may be configured to thicken a width of the vector as the second sampling interval is larger.

In the fluid analysis apparatus according to the present disclosure, the image may be a three-dimensional image obtained by imaging the subject by three-dimensional cine phase contrast magnetic resonance imaging, and the processor may be configured to derive, as the fluid information, a flow velocity vector of the fluid obtained by analyzing the three-dimensional image.

In the fluid analysis apparatus according to the present disclosure, the processor may be configured to derive, as the fluid information, a flow velocity vector of the fluid obtained by simulating the flow of the fluid by an analysis using computational fluid dynamics.

In the fluid analysis apparatus according to the present disclosure, the tubular structure may be a blood vessel, and the fluid may be blood.

In a fluid analysis method according to the present disclosure, an image obtained by imaging a subject including a tubular structure in which a fluid flows is analyzed, thereby deriving fluid information regarding flow of the fluid at each of pixel positions in the tubular structure;

within the tubular structure included in the image, a matching degree between the fluid information at a plurality of pixel-of-interest positions set at a first sampling interval and the fluid information at a plurality of pixel positions within a predetermined region based on the pixel-of-interest positions is derived;

a second sampling interval for displaying the fluid information is set in accordance with the matching degree; and the fluid information is sampled at the set second sampling interval, and a display is caused to display the fluid information.

Note that a program for causing a computer to execute the fluid analysis method according to the present disclosure may also be provided.

According to the present disclosure, the fluid information can be displayed at an appropriate sampling interval without imposing a load on a user.

BRIEF DESCRIPTION OF THE DRAWINGS

FIG. 5 is a diagram illustrating a table in which a size of a cross section and the first sampling interval are associated with each other;

DESCRIPTION OF THE PREFERRED EMBODIMENTS

Figure 1:
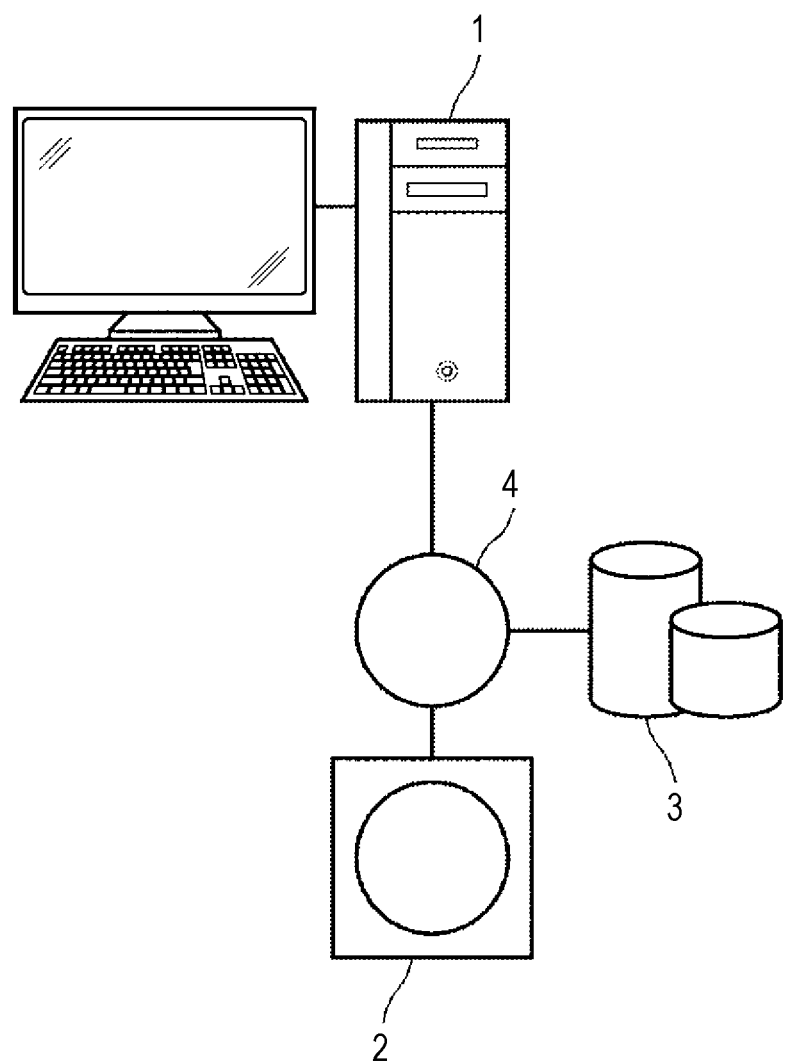
FIG. 1 is a hardware configuration diagram illustrating an overall diagnosis support system to which a fluid analysis apparatus according to an embodiment of the present disclosure is applied.

Now, an embodiment of the present disclosure will be described with reference to the drawings. FIG. 1 is a hardware configuration diagram illustrating an overall diagnosis support system to which a fluid analysis apparatus according to the embodiment of the present disclosure is applied. As illustrated in FIG. 1, in the diagnosis support system, a fluid analysis apparatus 1 according to this embodiment, a three-dimensional imaging apparatus 2, and an image storage server 3 are communicably connected via a network 4.

The three-dimensional imaging apparatus 2 is an apparatus that images a diagnosis-target body part of a subject thereby generating a three-dimensional image representing the body part. Specifically, the three-dimensional imaging apparatus 2 is a CT apparatus, an MM apparatus, a positron emission tomography (PET) apparatus, or the like. A three-dimensional image generated by the three-dimensional imaging apparatus 2 is transmitted to the image storage server 3 and is stored therein. Although this embodiment describes a case of acquiring a three-dimensional image of the aorta of a patient, the present disclosure is not limited to this, and the three-dimensional image may be an image of another blood vessel. In addition, in this embodiment, the three-dimensional imaging apparatus 2 is an MRI apparatus, and an MM image obtained by imaging a subject by three-dimensional cine phase contrast magnetic resonance imaging in the MRI apparatus is acquired as a three-dimensional image G0. However, the type of the three-dimensional image to be acquired is not limited to this. In addition, the aorta corresponds to a tubular structure in the present disclosure, and blood corresponds to a fluid in the present disclosure.

The image storage server 3 is a computer that stores and manages various types of data and includes an external mass storage device and database management software. The image storage server 3 communicates with the other apparatuses via the network 4 by wire or wirelessly to transmit and receive image data or the like. Specifically, the image storage server 3 acquires various types of data including image data of a three-dimensional image generated by the three-dimensional imaging apparatus 2 via the network and stores the image data in a recording medium such as the external mass storage device to manage the image data. Note that the form of storage of image data and communication between the apparatuses via the network 4 conform to a protocol such as Digital Imaging and Communication in Medicine (DICOM).

The fluid analysis apparatus 1 is a single computer in which a fluid analysis program according to the present disclosure is installed. The computer may be a workstation or a personal computer that a physician who performs diagnosis directly operates, or may be a server computer connected to the work station or personal computer via the network. The fluid analysis program is stored in a storage device of the server computer connected to the network or a network storage in an externally accessible state, is downloaded to a computer used by a physician on demand, and is installed. Alternatively, the fluid analysis program is recorded on a recording medium such as a digital versatile disc (DVD) or a compact disc read only memory (CD-ROM), is distributed, and is installed in a computer from the recording medium.

Figure 2:
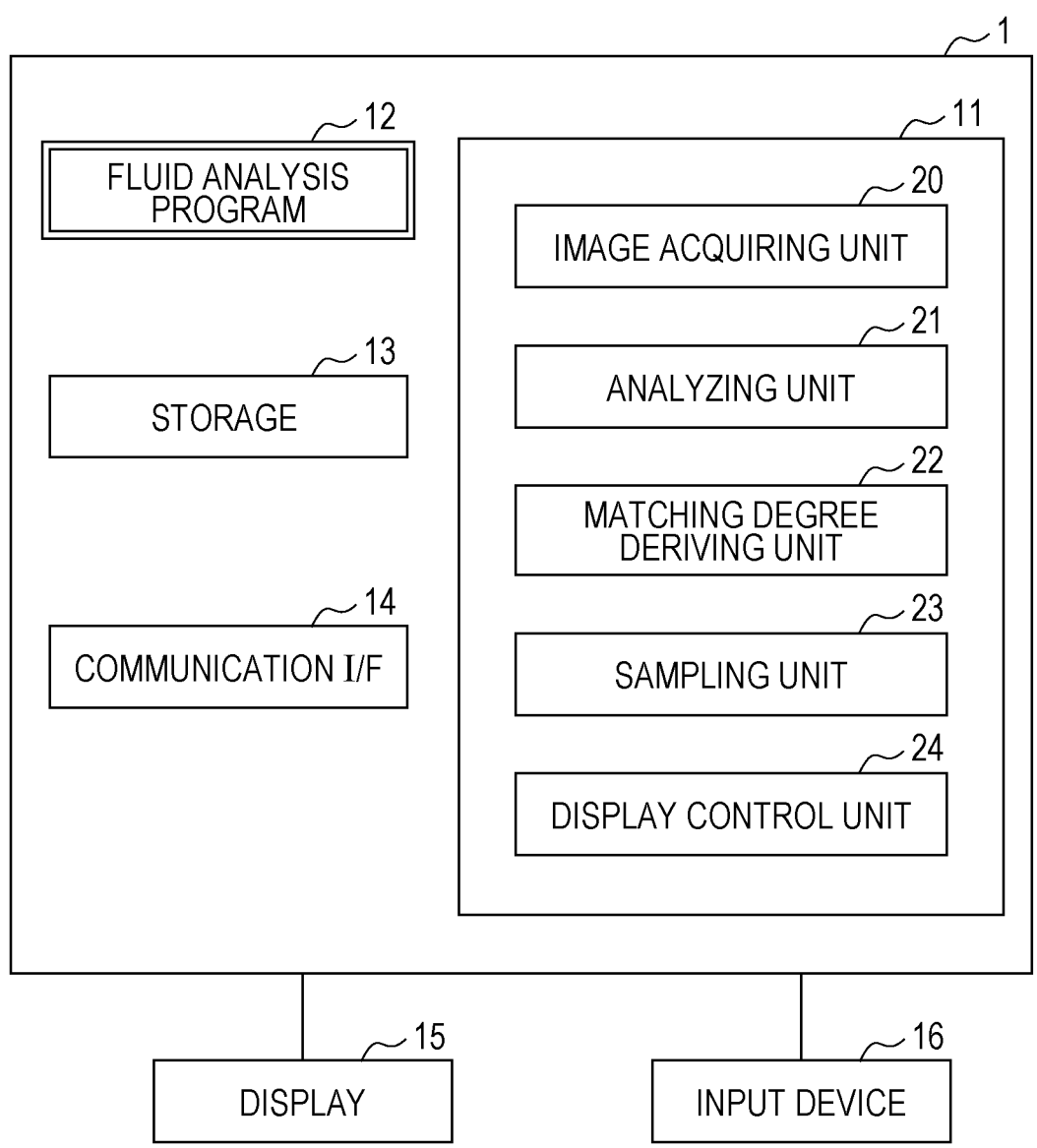
FIG. 2 is a diagram illustrating a schematic configuration of the fluid analysis apparatus according to the embodiment of the present disclosure.

FIG. 2 is a diagram illustrating a schematic configuration of the fluid analysis apparatus implemented by the fluid analysis program being installed in a computer. As illustrated in FIG. 2, the fluid analysis apparatus 1 includes a central processing unit (CPU) 11, a memory 12, a storage 13, and a communication interface (I/F) 14 as a configuration of a standard workstation. In addition, a display 15 such as a liquid crystal display and an input device 16 including a keyboard and a mouse are connected to the fluid analysis apparatus 1. The CPU 11 corresponds to a processor.

The storage 13 is constituted by a storage device such as a hard disk drive or a solid state drive (SSD) and stores various types of information including a three-dimensional image acquired from the image storage server 3 via the network 4 and information necessary for processing.

The communication I/F 14 is a network interface for controlling transmission of various types of information between the fluid analysis apparatus 1 and an external apparatus such as the image storage server 3 via the network 4.

The memory 12 stores a fluid analysis program according to the embodiment. As processes to be executed by the CPU 11, the fluid analysis program prescribes an image acquiring process for acquiring the three-dimensional image G0 obtained by the three-dimensional imaging apparatus 2 imaging a subject; an analyzing process for analyzing the three-dimensional image G0 and deriving fluid information regarding blood flow at each of pixel positions in the aorta; a matching degree deriving process for deriving, within the aorta included in the three-dimensional image G0, a matching degree between fluid information at a plurality of pixel-of-interest positions set at first sampling intervals and fluid information at a plurality of pixel positions within a predetermined region based on the pixel-of-interest positions; a sampling process for setting a second sampling interval for displaying the fluid information in accordance with the matching degree; and a display control process for sampling the fluid information at the set second sampling interval and displaying the fluid information on the display 15.

By the CPU 11 executing these processes in accordance with the program, the computer functions as an image acquiring unit 20, an analyzing unit 21, a matching degree deriving unit 22, a sampling unit 23, and a display control unit 24.

The image acquiring unit 20 acquires the three-dimensional image G0 from the image storage server 3. Note that, if the three-dimensional image G0 is already stored in the storage 13, the image acquiring unit 20 may acquire the three-dimensional image G0 from the storage 13.

The analyzing unit 21 analyzes the three-dimensional image G0 and derives fluid information R0 regarding blood flow at each of pixel positions in the aorta. In this embodiment, the analyzing unit 21 first extracts a blood vessel region from the three-dimensional image G0. Specifically, the analyzing unit 21 performs a multiresolution analysis on the three-dimensional image G0, performs an eigenvalue analysis of the Hessian matrix on images with different resolutions, and integrating the analysis results of the images with different resolutions, thereby extracting, as the blood vessel region, a region of the aortic arch as an aggregate of linear structures (blood vessels) with various sizes in a heart region included in the three-dimensional image G0 (for example, see Y Sato, et al., "Three-dimensional multi-scale line filter for segmentation and visualization of curvilinear structures in medical images", Medical Image Analysis, June 1998, Vol. 2, No. 2, p.p. 143-168). Furthermore, the analyzing unit 21 may couple center points of the extracted linear structures by using a minimum spanning tree algorithm or the like to generate tree-structure data representing the aorta, and then, may obtain a cross section orthogonal to a core wire at each point (node of tree-structure data) on the core wire obtained by connecting the center points of the extracted aorta, recognize the outline of the aorta by using a known segmentation method such as graph cuts on each cross section, and associate information representing the outline to a corresponding node of the tree-structure data, thereby extracting a region of the aorta as the blood vessel region.

Note that the method for extracting the blood vessel region is not limited to the above method, and another known method such as region expansion may also be used.

Subsequently, the analyzing unit 21 derives a flow velocity vector at each voxel position in the blood vessels as the fluid information R0 by using velocity information in the blood vessel region extracted from the three-dimensional image G0.

Figure 3:
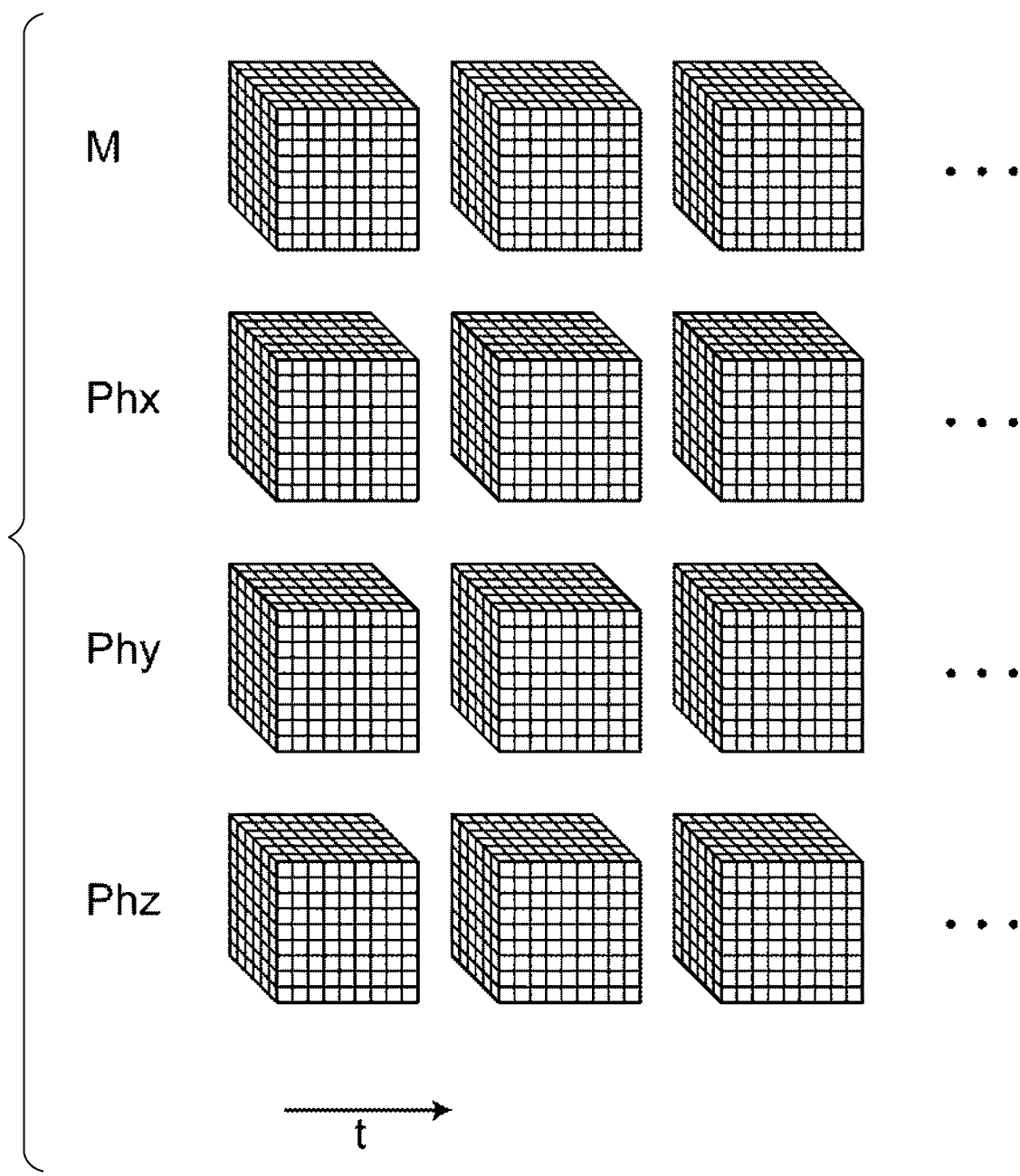
FIG. 3 is a diagram illustrating a three-dimensional image captured by three-dimensional cine phase contrast magnetic resonance imaging.

FIG. 3 is a diagram illustrating the three-dimensional image G0 captured by three-dimensional cine phase contrast magnetic resonance imaging. As illustrated in FIG. 3, image data of the three-dimensional image G0 captured by three-dimensional cine phase contrast magnetic resonance imaging includes three-dimensional data of magnitude data M, X-axis-direction phase data Phx, Y-axis-direction phase data Phy, and Z-axis-direction phase data Phz obtained in a predetermined cycle (e.g., cardiac cycle) along time t. The X-axis-direction phase data Phx, the Y-axis-direction phase data Phy, and the Z-axis-direction phase data Phz are generated by encoding (velocity encoding: VENC) the magnitude data M in the X-axis direction, the Y-axis direction, and the Z-axis direction. The X-axis-direction phase data Phx, the Y-axis-direction phase data Phy, and the Z-axis-direction phase data Phz are data representing the flow velocity in the respective axis directions. From the three kinds of phase data, the analyzing unit 21 derives a three-dimensional flow velocity vector (hereinafter referred to as flow velocity vector) at each voxel position of the three-dimensional image G0 as the fluid information R0.

Note that the image acquiring unit 20 may acquire three-dimensional ultrasound images obtained in a time-series manner by Doppler measurement and may acquire flow velocity vectors by using the velocity information in the blood vessel region obtained on the basis of the ultrasound images to derive the fluid information R0.

The matching degree deriving unit 22 derives, within the aorta included in the three-dimensional image G0, a matching degree between fluid information at a plurality of pixel-of-interest positions set at a first sampling interval and fluid information at a plurality of pixel positions within a predetermined region based on the pixel-of-interest positions. Thus, the matching degree deriving unit 22 first sets the first sampling interval that is a sampling interval for setting the pixel-of-interest positions. In this embodiment, the analyzing unit 21 sets the first sampling interval for setting the pixel-of-interest positions in accordance with the size of a region intersecting the center line using, as the center line, a core line derived when the blood vessel region is extracted.

Figure 4:
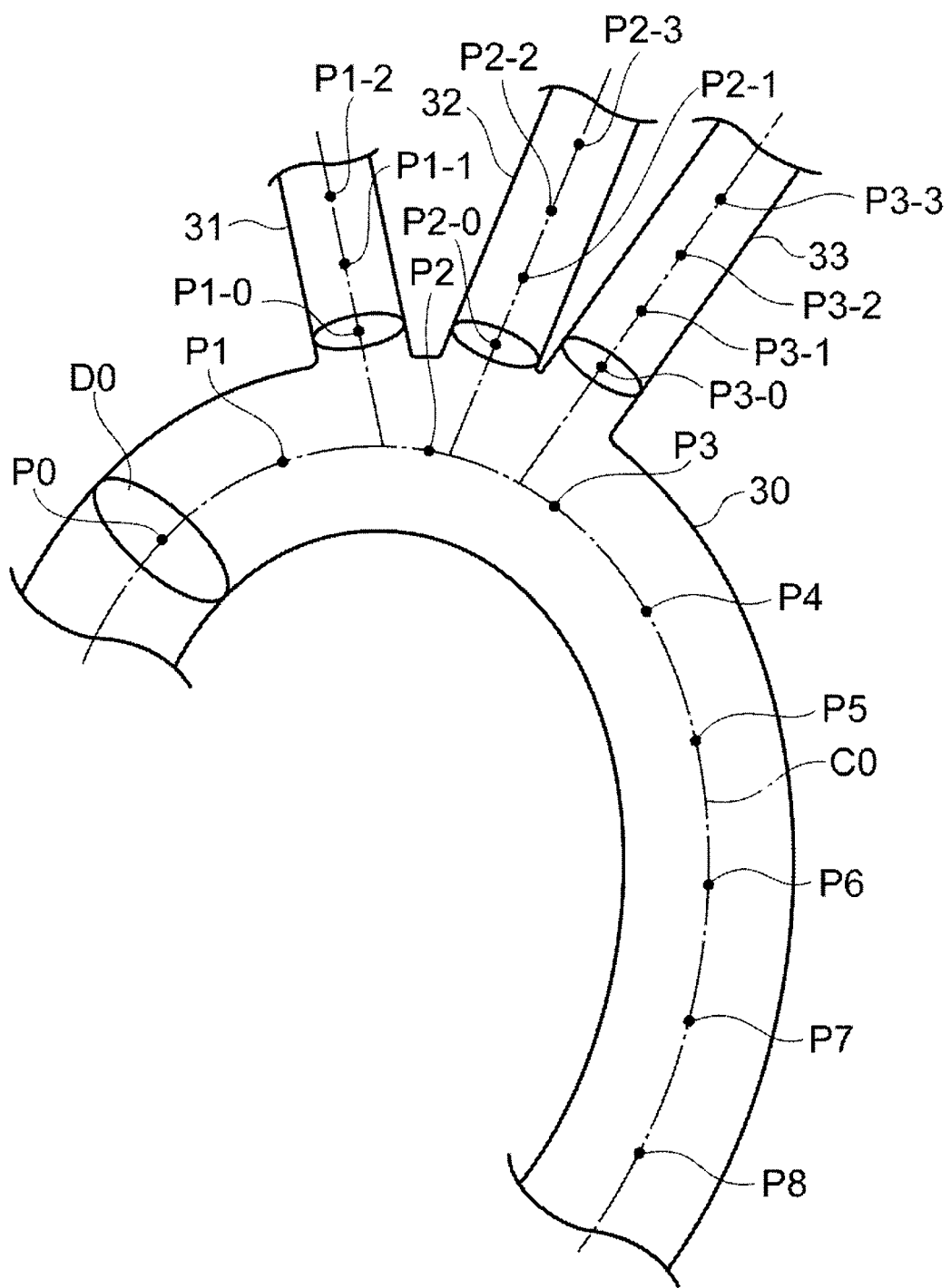
FIG. 4 is a diagram for describing setting of a first sampling interval.

FIG. 4 is a diagram for describing setting of the first sampling interval. Note that FIG. 4 illustrates an aortic arch 30, a brachiocephalic artery 31, a left common carotid artery 32, and a left subclavian artery 33 in the extracted aorta. As illustrated in FIG. 4, the matching degree deriving unit 22 first sets a cross section D0 intersecting a center line C0 of the aortic arch 30 at a predetermined initial reference position P0. Specifically, the matching degree deriving unit 22 defines the cross section D0 that is a region orthogonal to the center line C0. Note the initial reference position P0 may be set in the following manner. The display 15 displays a volume-rendering image or the like of the extracted aorta, and an operator designates the initial reference position P0 on the displayed image of the aorta by using the input device 16.

Subsequently, the matching degree deriving unit 22 derives the size of the cross section D0. As the size of the cross section D0, the diameter or radius of the cross section D0, the area of the cross section D0, or the volume of a predetermined thickness including the cross section D0 may be used. The thickness may be 1 mm, for example, but is not limited to this.

Subsequently, on the basis of the initial reference position P0, the matching degree deriving unit 22 sets each of a plurality of reference positions Pk (k=1 to n) for setting the first sampling interval along the center line C0 at a predetermined interval. The predetermined interval may be any given interval, such as 5 mm, 1 cm, or 3 cm. Then, the size of a cross section Dk is derived at each of the reference positions Pk.

In a similar manner, the matching degree deriving unit 22 also sets initial reference positions P1-0, P2-0, and P3-0 for the brachiocephalic artery 31, the left common carotid artery 32, and the left subclavian artery 33, sets reference positions P1-1, P1-2 . . . , P2-1, P2-2 . . . , P3-1, P3-2 . . . at predetermined intervals, and derives the sizes of cross sections at the initial reference positions and the reference positions.

Subsequently, in accordance with the size of the cross section Dk, the matching degree deriving unit 22 sets the first sampling interval for setting the pixel-of-interest positions. Specifically, the smaller the cross section Dk is, the smaller the sampling interval is. In this embodiment, as illustrated in FIG. 5, a table LUT1 in which the size of the cross section Dk and the first sampling interval are associated with each other is stored in the storage 13. Although the size of the cross section Dk is the diameter in FIG. 5, the size of the cross section Dk may also be the radius, the area, or the volume. In addition, "0 to 10" in FIG. 5 indicates that the diameter is greater than 0 mm and less than or equal to 10 mm. Furthermore, the numerical value of the first sampling interval denotes the number of pixels that are present between pixels at which the fluid information R0 is to be displayed. Since the diameter of the aorta is about 35 mm at most, the table LUT1 illustrates the sizes up to 35 mm. As illustrated in FIG. 5, in the table LUT1, the size of the cross section Dk increments by 5 mm, while the sampling interval increments by 2 pixels. With reference to the table LUT1, the matching degree deriving unit 22 sets the first sampling interval in accordance with the size of the cross section Dk. Note that the first sampling interval is not limited to the values illustrated in the table LUT1.

Instead of setting the first sampling interval with reference to the table LUT1, the first sampling interval may be set in proportion to the size of the cross section Dk.

The first sampling interval herein is a three-dimensional sampling interval in the three-dimensional image G0. However, a two-dimensional sampling interval may also be set on the assumption that a two-dimensional cross section in the aorta is displayed.

Figure 6:
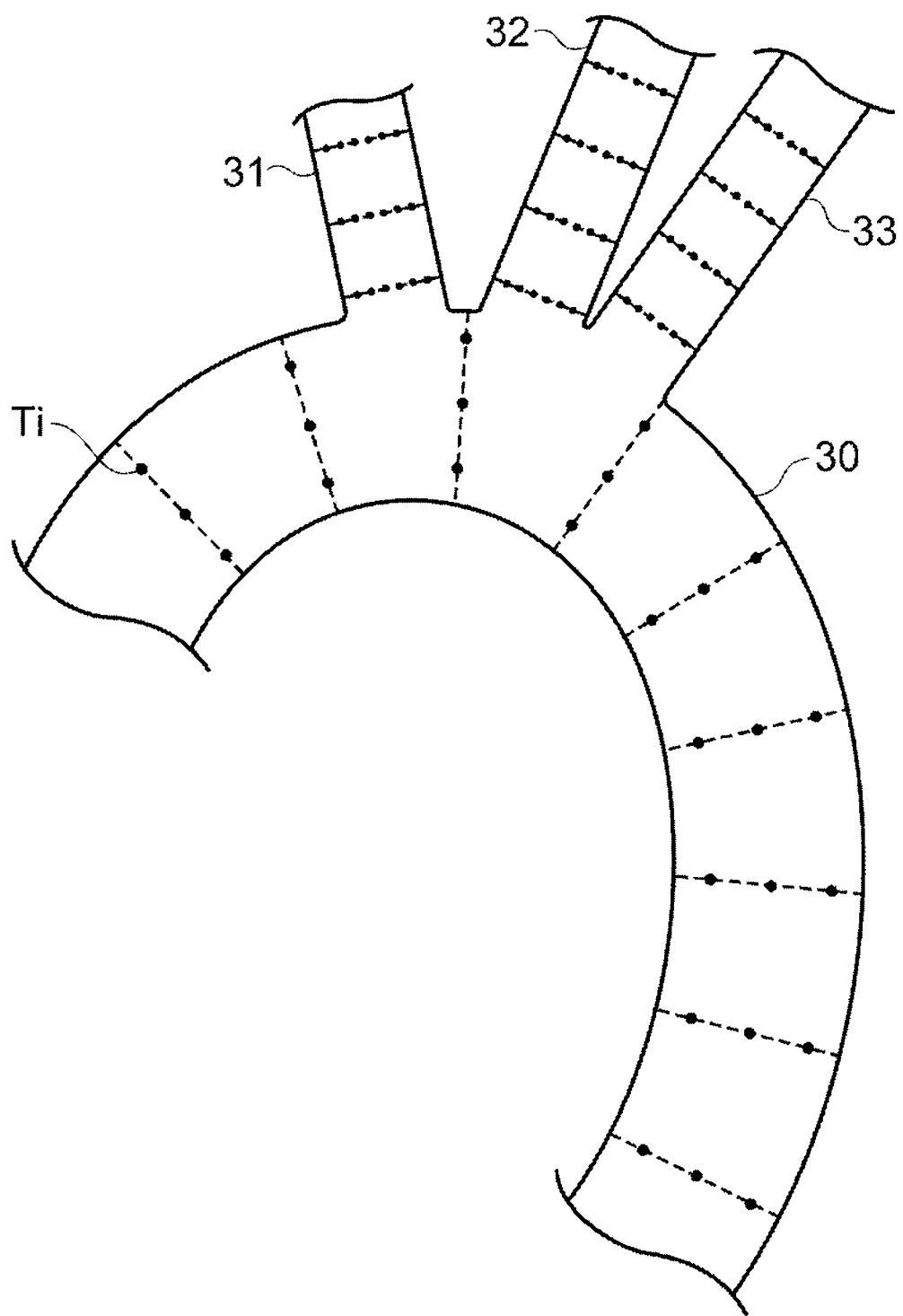
FIG. 6 is a diagram illustrating pixel-of-interest positions.

Subsequently, the matching degree deriving unit 22 sets the pixel-of-interest positions at the set first sampling interval. FIG. 6 is a diagram illustrating the pixel-of-interest positions. Note that FIG. 6 illustrates pixel-of-interest positions Ti by black points.

The matching degree deriving unit 22 further sets a region having a predetermined size based on each of the pixel-of-interest positions Ti. Although the region is, for example, 10×10×10 pixels whose center is the pixel-of-interest position Ti, the present disclosure is not limited to this. In addition, as the region, for example, a spherical region or a polyhedral region whose center is the pixel-of-interest position Ti may also be set. Furthermore, as in a case where the first sampling interval is set, a larger region may be set as the cross section Dk is larger.

The matching degree deriving unit 22 derives a matching degree E0 between fluid information Rt at the pixel-of-interest positions Ti and fluid information Rj (j is the number of other pixel positions) at other pixel positions other than the pixel-of-interest positions within the set region. The matching degree E0 herein represents a matching degree of the fluid information, that is, a matching degree of the direction between flow velocity vectors or a matching degree of the direction and magnitude therebetween. In this embodiment, as the matching degree E0, a matching degree of the direction between pieces of fluid information is used. Thus, the matching degree deriving unit 22 derives, as Ej, a cosine similarity between each piece of the fluid information Rt and each piece of the fluid information Rj. The cosine similarity is a value of a cosine of an angle formed by flow velocity vectors that are pieces of the fluid information R0, and is a value of greater than or equal to −1 and less than or equal to 1. In addition, the matching degree deriving unit 22 derives the sum total of the cosine similarity Ej between each piece of the fluid information Rt and each piece of the fluid information Rj, and derives the average of the derived sum total within the region as the matching degree E0. Thus, the matching degree E0 is represented by the following Formula (1). In Formula (1), N is the number of pixel positions other than the pixel-of-interest positions Ti within the region. Instead of Formula (1), as illustrated in Formula (2), the matching degree E0 may be derived by weighting the cosine similarity Ej by a weight wj in accordance with the distance of the pixel positions other than the pixel-of-interest positions Ti from the pixel-of-interest positions Ti within the region.

$$E0=(\Sigma Ej)/N \tag{1}$$

$$E0=(\Sigma Ej \times wj)/\Sigma wj \tag{2}$$

On the other hand, in a case where the matching degree of the direction and magnitude between pieces of fluid information is used as the matching degree E0, the matching degree deriving unit 22 derives a difference Dj of the direction and magnitude between each piece of the fluid information Rt and each piece of the fluid information Rj, according to Dj=|Rj−Rt|/|Rt|. In addition, as in Formula (3) below, the matching degree deriving unit 22 derives the average of the sum total of the difference Dj within the region as the matching degree E0. In Formula (3), N is the number of pixel positions other than the pixel-of-interest positions Ti within the region. Instead of Formula (3), as illustrated in Formula (4), the matching degree E0 may be derived by weighting the difference Dj by the weight wj in accordance with the distance of the pixel positions other than the pixel-of-interest positions Ti from the pixel-of-interest positions Ti within the region.

$$E0=(\Sigma Dj)/N \tag{3}$$

$$E0=(\Sigma Dj \times wj)/\Sigma wj \tag{4}$$

In accordance with the matching degree E0 derived by the matching degree deriving unit 22, The sampling unit 23 sets a second sampling interval for displaying the fluid information R0. Specifically, the second sampling interval that is larger is set as the matching degree E0 is larger. In this embodiment, for example, the matching degree E0 is compared with predetermined thresholds Th1 and Th2 (Th1>Th2), and, if the matching degree E0 is greater than or equal to the threshold Th1, the second sampling interval is set to the first sampling interval. If the matching degree E0 is greater than or equal to the threshold Th2 and less than the threshold Th1, the second sampling interval is set to ½ of the first sampling interval, and the number of pixel positions at which the fluid information R0 is to be displayed within the region is doubled. If the matching degree E0 is less than the threshold Th2, the second sampling interval is set to ⅓ of the first sampling interval, and the number of pixel positions at which the fluid information R0 is to be displayed within the region is tripled. Herein, the direction in which the sampling interval is narrowed, that is, the direction in which pixel positions at which the fluid information R0 is to be displayed is increased may be, for example, the diameter direction of a cross section intersecting the center line C0 of the aortic arch 30, or may be the direction of the center line C0. Note that the number of thresholds is not limited to two, and only a single threshold or three or more thresholds can also be set. In addition, the relationship between the second sampling interval and the thresholds is not limited to the above relationship, and any relationship can be set. Note that the relationship between the second sampling interval and the thresholds may be stored in the storage 13.

Figure 7:
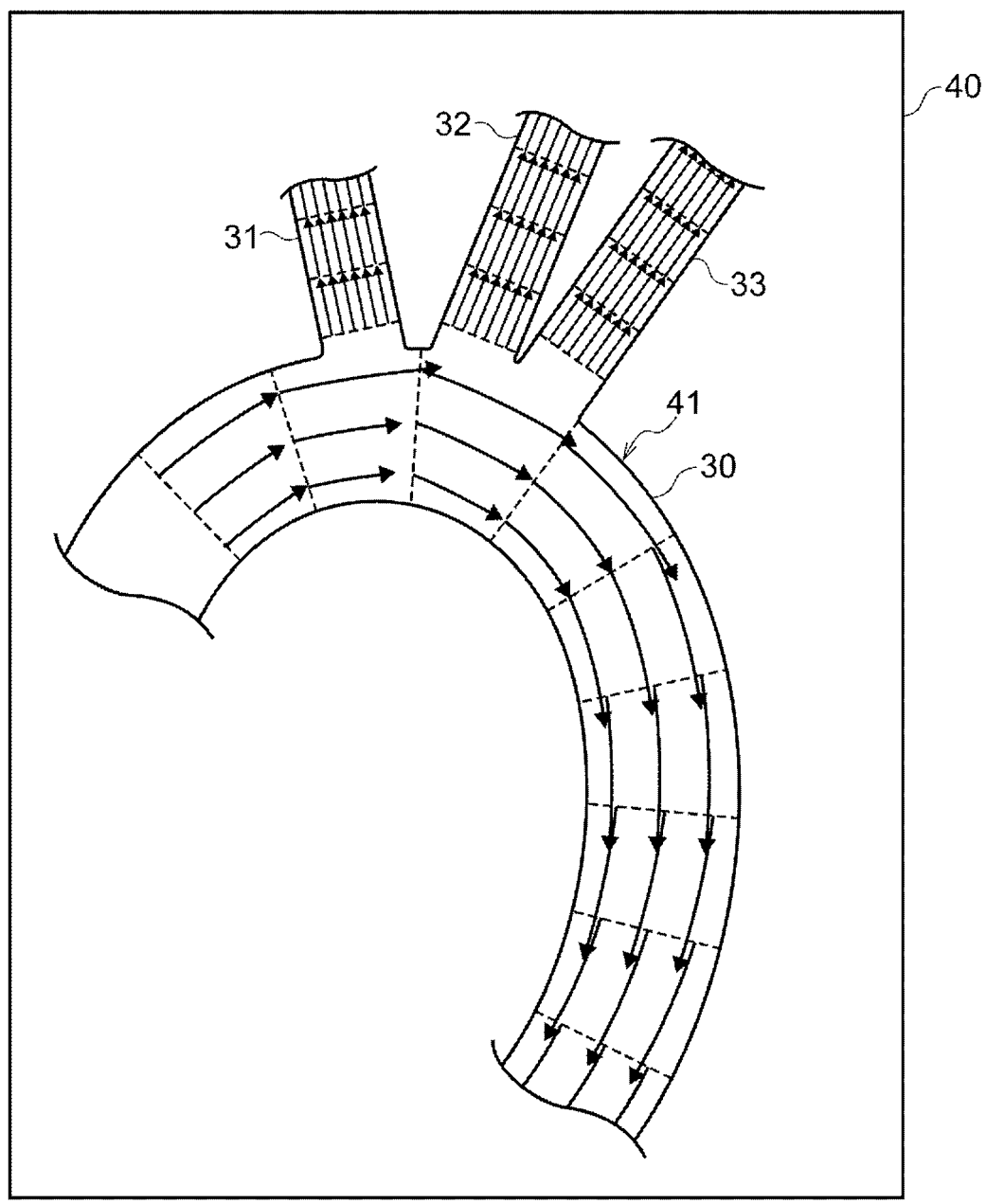
FIG. 7 is a diagram illustrating a display screen of fluid information.

The display control unit 24 samples the fluid information R0 at the second sampling interval set by the sampling unit 23 and causes the display 15 to display the fluid information R0. FIG. 7 is a diagram illustrating a display screen of the fluid information R0 displayed on the display 15. As illustrated in FIG. 7, on a display screen 40, a region 41 including the brachiocephalic artery 31, the left common carotid artery 32, the left subclavian artery 33, and the aortic arch 30 is displayed. From a cross section orthogonal to a reference position in FIG. 4 in the region 41 as a starting point, the fluid information R0 is sampled at the second sampling interval set by the sampling unit 23 and displayed. Although FIG. 7 illustrates a two-dimensional image of the aortic arch 30, the brachiocephalic artery 31, the left common carotid artery 32, and the left subclavian artery 33 for description, actually, the aortic arch 30, the brachiocephalic artery 31, the left common carotid artery 32, and the left subclavian artery 33 is displayed three-dimensionally by a method such as volume rendering or the like.

Note that the fluid information R0 to be displayed is representative fluid information of all pieces of the fluid information R0 within the region in which the matching degree E0 is derived. For example, if the matching degree E0 is greater than or equal to the threshold Th1 and the first sampling interval and the second sampling interval match each other, the fluid information R0 is displayed only at the pixel-of-interest positions Ti. In this case, the fluid information R0 is the representative value of all pieces of the fluid information R0 within the region. On the other hand, if the matching degree E0 is less than the threshold Th1 and a plurality of pieces of the fluid information R0 are to be displayed within the region, the fluid information R0 may be the representative value of the fluid information R0 within a predetermined region including the pixel positions at which the fluid information R0 is to be displayed. For example, if the number of the pixel positions at which the fluid information R0 is to be displayed is three within the region in which the matching degree E0 is derived, the region in which the matching degree E0 is derived may be divided into three regions, and the representative value of the fluid information R0 in each of the divided regions may be displayed. The representative value may be the fluid information R0 at the pixel positions at which the fluid information R0 is to be displayed, the average value of all pieces of the fluid information R0 within the region, a weighted average value obtained by weighting a larger weight as the distance to the pixel positions at which the fluid information R0 is to be displayed is shorter, a median, a minimum, a maximum, or the like.

Here, if the matching degree E0 is large, within the region based on the pixel-of-interest positions Ti, the fluid information R0 is uniform. For example, if there is no abnormality such as an aneurysm in the aortic arch 30, the direction and magnitude of the blood flow is uniform unless the thickness of blood vessel changes. Thus, the second sampling interval set by the sampling unit 23 matches the first sampling interval. Therefore, as illustrated in FIG. 7, the fluid information R0 is displayed only at the pixel-of-interest positions Ti. Note that in FIG. 7, the sampling interval in the direction in which the center line C0 extends is an interval between reference positions.

Figure 8:
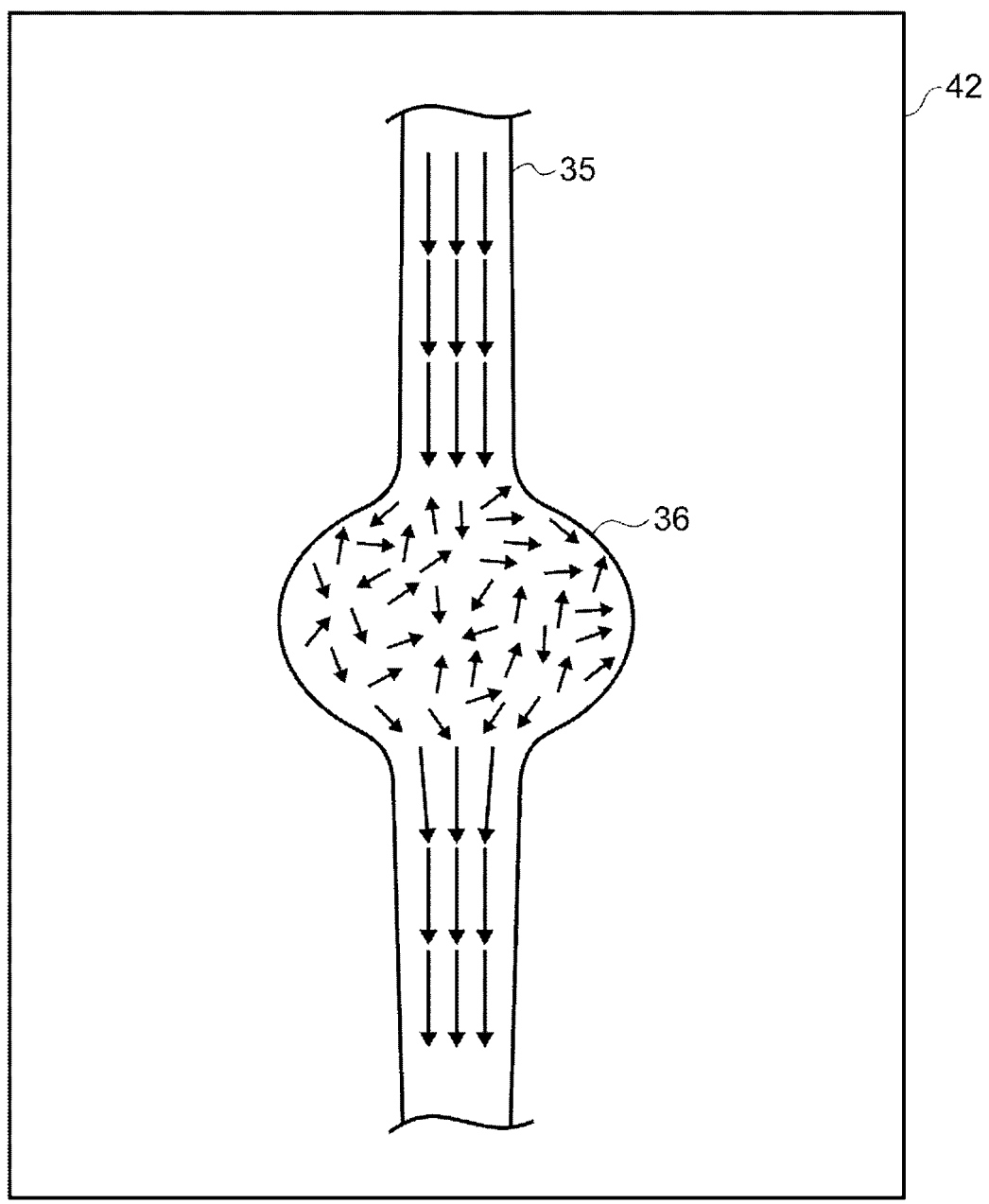
FIG. 8 is a diagram illustrating a display screen of fluid information.

On the other hand, if there is an aortic aneurysm in the aorta, within the aortic aneurysm, the direction and magnitude of the blood flow, that is, the fluid information R0, are at random. Thus, within the aortic aneurysm, the matching degree E0 derived by the matching degree deriving unit 22 becomes smaller. Accordingly, the sampling unit 23 sets the second sampling interval that is smaller than the first sampling interval within the aortic aneurysm. A display screen of the fluid information R0 in such a case is illustrated in FIG. 8. On a display screen 42 illustrated in FIG. 8, in a case where an aortic aneurysm 36 is present in an abdominal aorta 35, in portions other than the aortic aneurysm 36, as in FIG. 7, the second sampling interval matches the first sampling interval. On the other hand, in the aortic aneurysm 36, the fluid information R0 is displayed such that the direction and magnitude are at random at sampling intervals smaller than the first sampling interval. Note that in FIG. 8, the sizes of arrows of the fluid information R0 within the aortic aneurysm 36 are fixed for simple illustration.

Figure 9:
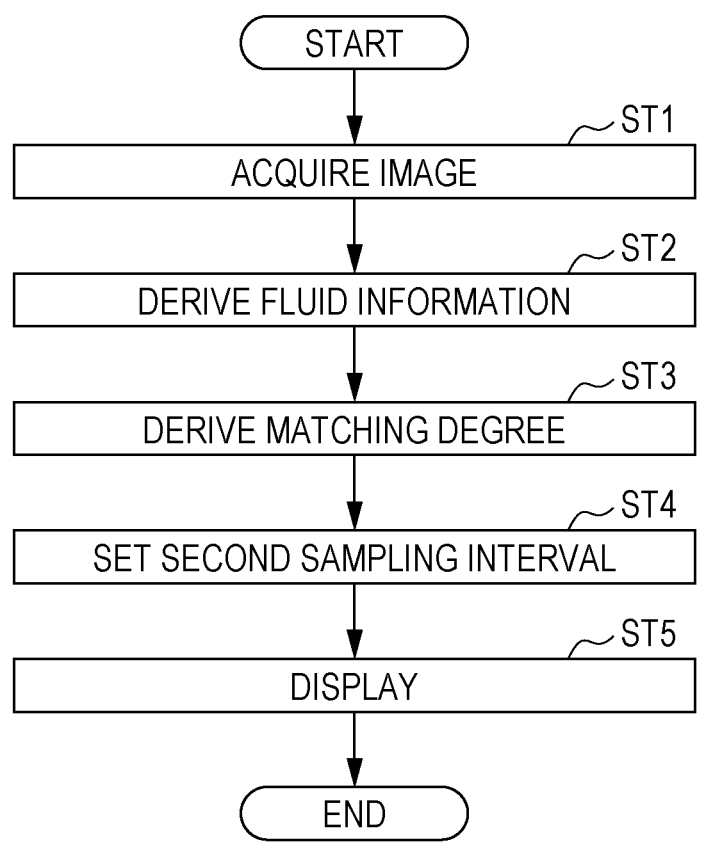
FIG. 9 is a flowchart illustrating a process performed in the embodiment.

Next, a process performed in this embodiment will be described. FIG. 9 is a flowchart illustrating the process performed in this embodiment. First, the image acquiring unit 20 acquires the three-dimensional image G0 from the image storage server 3 (acquire image; step ST1). Subsequently, the analyzing unit 21 analyzes the three-dimensional image G0 and derives the fluid information R0 regarding blood flow at each position in the blood vessels (step ST2). Subsequently, within the aorta included in the three-dimensional image G0, the matching degree deriving unit 22 derives the matching degree E0 between the fluid information Rt at the plurality of pixel-of-interest positions Ti set at the first sampling interval and the fluid information Rj at the plurality of pixel positions within the predetermined region based on the pixel-of-interest positions Ti (step ST3).

Subsequently, the sampling unit 23 sets the second sampling interval for displaying the fluid information R0 in accordance with the matching degree E0 (step ST4). Furthermore, the display control unit 24 samples the fluid information R0 at the set second sampling interval and causes the display 15 to display the fluid information R0 (step ST5), and the process ends.

In the above manner, in this embodiment, the second sampling interval for displaying the fluid information R0 is set in accordance with the matching degree E0 between the fluid information Rt at the pixel-of-interest positions Ti and the fluid information Rj at the plurality of pixel positions within the predetermined region based on the pixel-of-interest positions Ti, and the fluid information R0 is sampled at the set second sampling interval and displayed. Accordingly, the fluid information R0 can be displayed at an appropriate sampling interval without imposing a load on a user.

Figure 10:
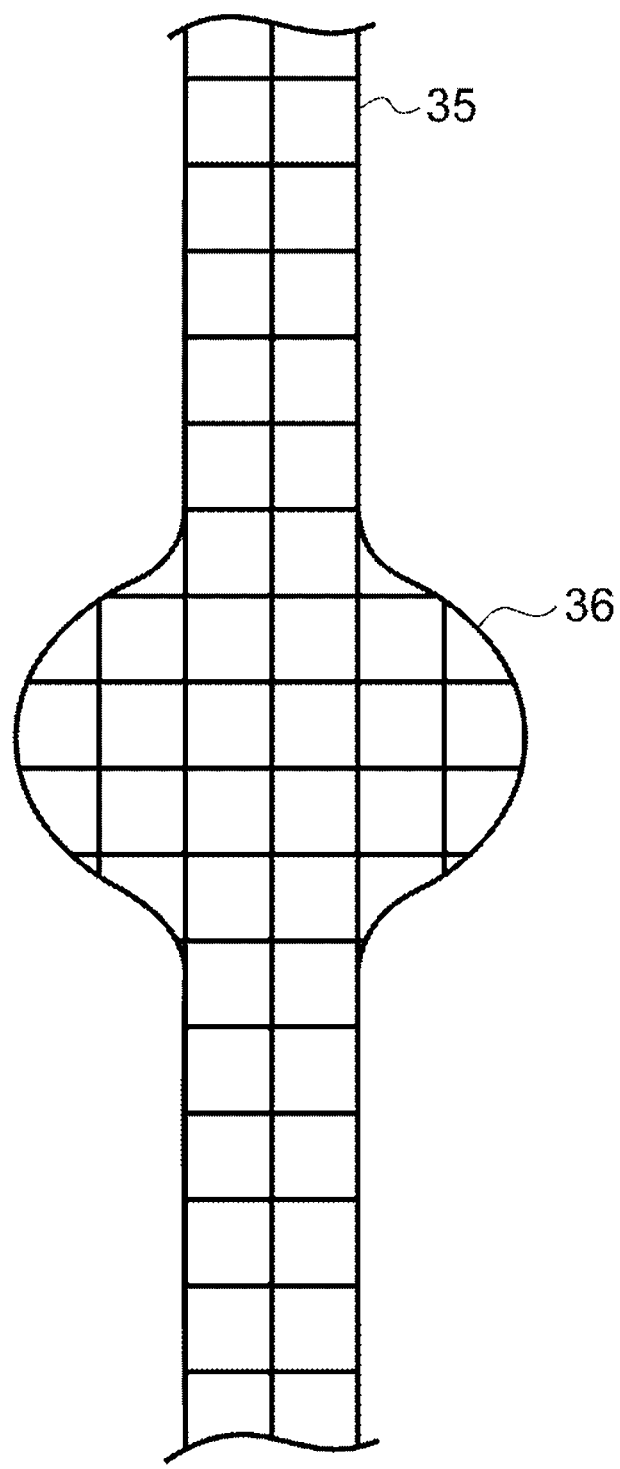
FIG. 10 is a diagram illustrating a region based on the pixel-of-interest positions in a case where the first sampling interval is set to a predetermined interval.

Although the first sampling interval for setting the pixel-of-interest positions is set in accordance with the size of a cross section passing through the center line C0 in the above embodiment, the present disclosure is not limited to this. The first sampling interval may be set to a predetermined interval. For example, in a case where the first sampling interval is set to a predetermined interval in the abdominal aorta 35 including the aortic aneurysm 36 as illustrated in FIG. 8, the region based on the pixel-of-interest positions is, for example, a rectangular (cubic) region at an equal interval as illustrated in FIG. 10.

Figure 11:
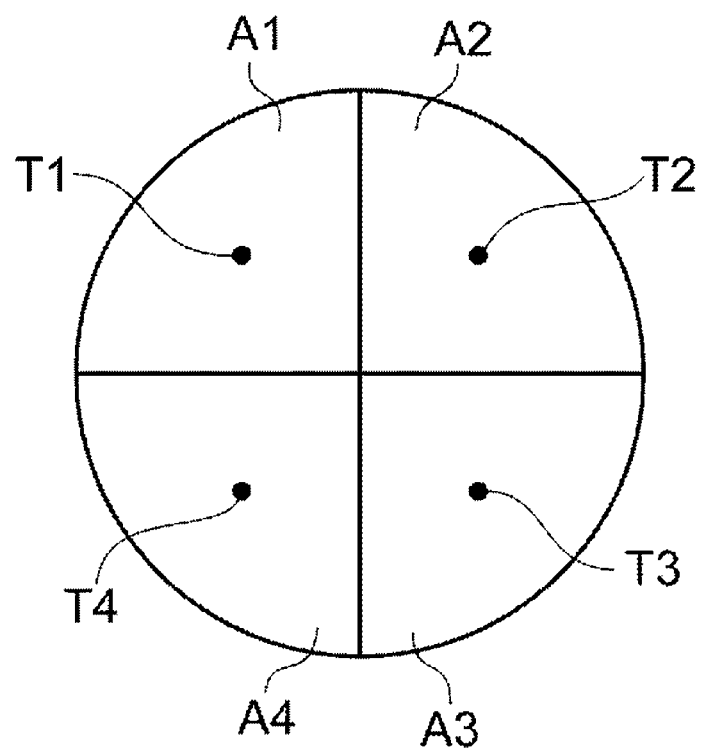
FIG. 11 is a cross-sectional view of a blood vessel.

In addition, although the second sampling interval is set in accordance with the matching degree E0 in the above embodiment, for example, if the matching degree E0 is less than the threshold Th1, the second sampling interval may be set further in accordance with the size of a region intersecting the center line. In this case, the second sampling interval that is larger may be set as the region intersecting the center line is larger. FIG. 11 is a cross-sectional view of a blood vessel. In FIG. 11, four pixel-of-interest positions T1 to T4 are set, and four regions A1 to A4 based on the pixel-of-interest positions T1 to T4 are set for description.

Here, if the matching degree E0 of the fluid information R0 is greater than or equal to the threshold Th1 in the regions A1 and A3, the second sampling interval in the regions A1 and A3 is the first sampling interval, which is the sampling interval between the pixel-of-interest positions T1 and T3.

On the other hand, if the matching degree E0 is small in the regions A2 and A4, the second sampling interval is set in accordance with the size of a cross section, and the fluid information R0 is displayed at the set second sampling interval. The displayed fluid information is illustrated in FIG. 12.

Figure 12:
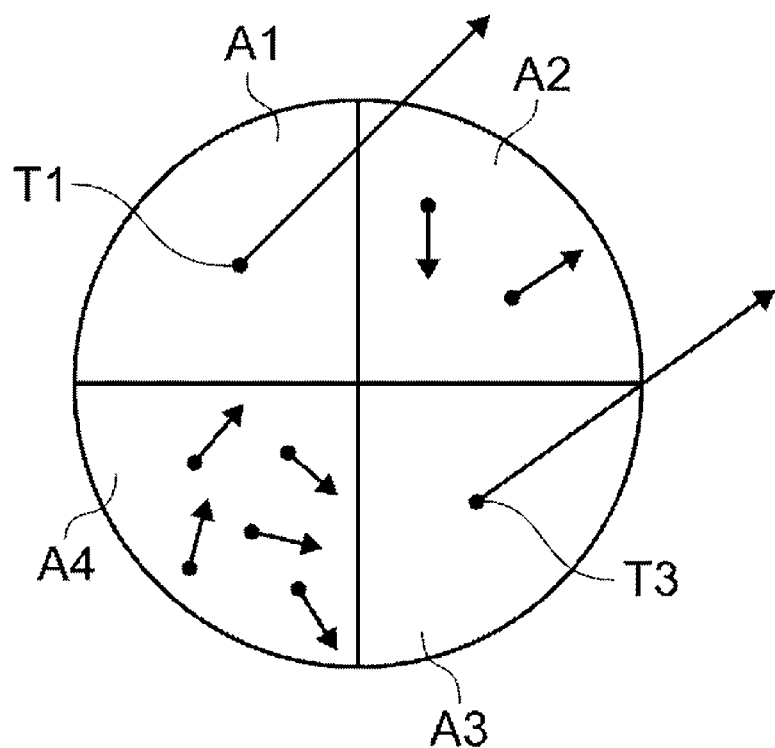
FIG. 12 is a diagram for describing fluid information displayed on the cross section illustrated in FIG. 11.
Figure 13:
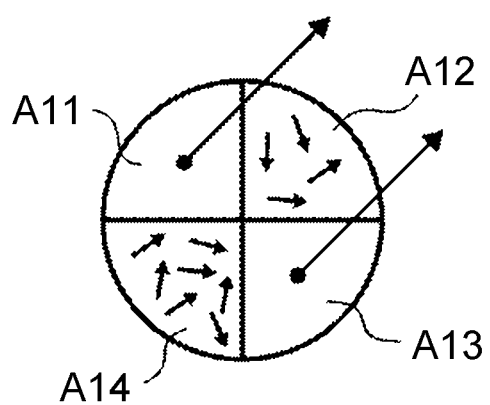
FIG. 13 is a diagram for describing fluid information displayed on a cross section smaller than that in FIG. 11.

On the other hand, an example of the fluid information R0 displayed for a blood vessel whose cross-sectional area is smaller than the blood vessel illustrated in FIGS. 11 and 12 is illustrated in FIG. 13. It is assumed that the matching degree E0 is greater than or equal to the threshold Th1 in regions A11 and A13 illustrated in FIG. 13, and the matching degree E0 is less than the threshold Th1 in regions A12 and A14. Since the cross section of the blood vessel illustrated in FIG. 13 is smaller than the cross section of the blood vessel illustrated in FIGS. 11 and 12, the sampling interval for displaying the fluid information R0 in the regions A12 and A14 is smaller than the sampling interval for displaying the fluid information R0 in the regions A2 and A4 illustrated in FIG. 11.

Note that the second sampling interval in accordance with the size of the region intersecting the center line may be an interval that can be preset by an operator. The set second sampling interval may be stored in the storage 13.

Although the interval between the predetermined reference positions as the first sampling interval in the direction in which the center line C0 of the blood vessel extends in the above embodiment, the present disclosure is not limited to this. In the direction in which the center line C0 of the blood vessel extends, the first sampling interval may be set in accordance with the size of the region intersecting the center line C0. Now, setting of the sampling interval in the direction in which the center line C0 extends will be described.

Figure 14:
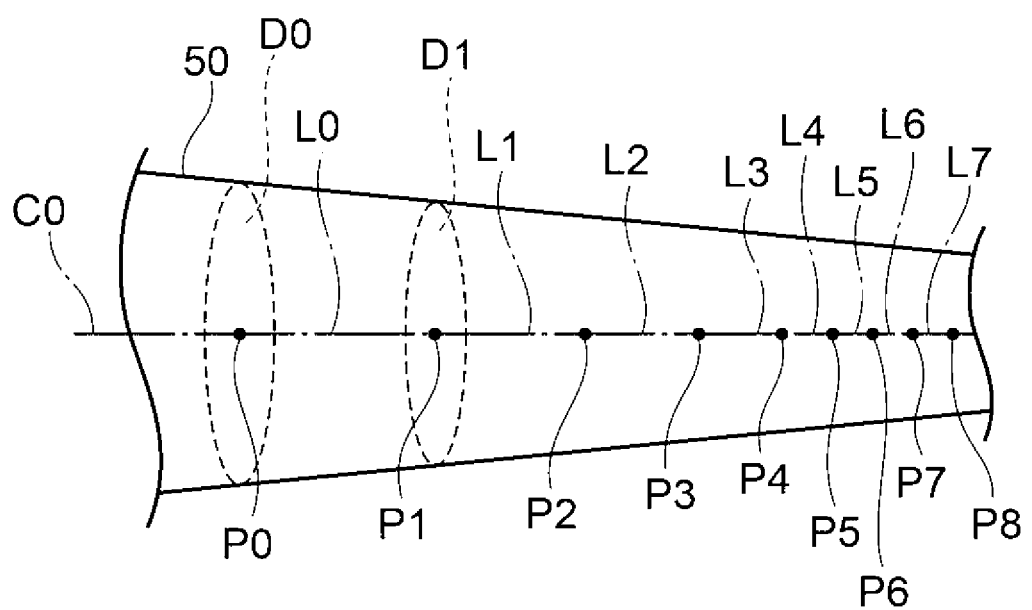
FIG. 14 is a diagram for describing setting of the first sampling interval in a direction in which a center line extends.

FIG. 14 is a diagram for describing setting of the first sampling interval in the direction in which the center line C0 extends. Note that FIG. 14 illustrates a blood vessel 50 whose diameter gradually decreases for the ease of description. In the blood vessel 50, the direction in which the diameter decreases is the downstream side of the blood flow. First, as illustrated in FIG. 14, on the basis of the initial reference position P0, the sampling unit 23 sets a next reference position P1 with a predetermined initial interval L0 interposed along the center line C0. The initial interval L0 is the sampling interval between the initial reference position P0 and the reference position P1. Note that the initial interval L0 may be any given interval, such as 5 mm, 1 cm, 3 cm, and the like.

Subsequently, the matching degree deriving unit 22 sets cross sections D0 and D1 at the initial reference position P0 and the reference position P1, respectively, and derives a ratio a1 of the size of the cross section D1 to the size of the cross section D0. The matching degree deriving unit 22 multiplies the initial interval L0 by the ratio a1, thereby determining an interval L1 between the reference position P1 and a next reference position P2. That is, the interval L1 is set according to L1=a1×L0. The interval L1 is the first sampling interval between the reference position P1 and the reference position P2. Herein, since D1<D0, L1<L0 is satisfied.

Subsequently, the matching degree deriving unit 22 sets a cross section D2 (not illustrated) at the reference position P2 and derives a ratio a2 of the size of the cross section D2 to the size of the cross section D1. The matching degree deriving unit 22 multiplies the interval L1 by the ratio a2, thereby determining an interval L2 between the reference position P2 and a next reference position P3. That is, the interval L2 is set according to L2=a2×L1. The interval L2 is the first sampling interval between the reference position P2 and the reference position P3. Herein, since D2<D1, L2<L1 is satisfied.

In a similar manner, the matching degree deriving unit 22 sets reference positions P3, P4, P5 . . . , thereby setting sampling intervals L3, L4, L5 . . . in the direction in which the center line C0 extends in the blood vessel 50. Thus, as illustrated in FIG. 14, as the blood vessel 50 becomes thinner, that is, as the region intersecting the center line C0 becomes smaller, the first sampling interval in the direction in which the center line C0 extends becomes smaller. That is, the relationship between the initial interval L0 and the first sampling intervals L1 to L5 is L5<L4<L3<L2<L1<L0.

If the first sampling interval in the direction in which the center line C0 extends becomes too small, in a case where the second sampling interval matches the first sampling interval, the displayed fluid information R0 is difficult to view. Thus, if the first sampling interval becomes less than or equal to a predetermined threshold, the first sampling interval in the direction in which the center line C0 extends may be fixed. In FIG. 14, sampling intervals L5 to L7 are fixed.

Figure 15:
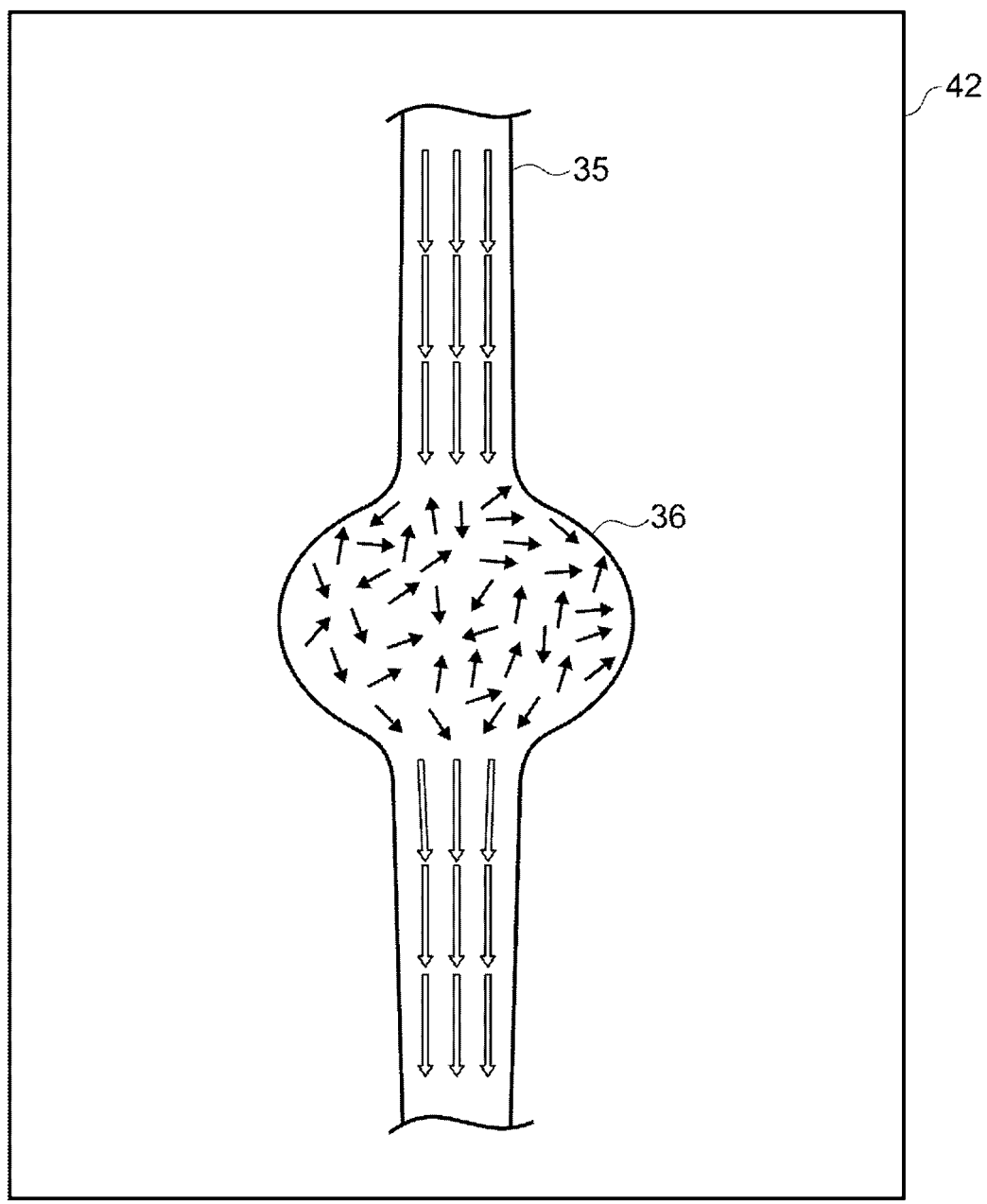
FIG. 15 is a diagram illustrating a display screen of fluid information.

Since the second sampling interval is smaller as the matching degree E0 is larger in the above embodiment, in a blood vessel including many regions where the matching degree E0 is large, that is, in a blood vessel in which the regions where the matching degree E0 is large is dominant, the fluid information R0 to be displayed becomes sparse. In this case, even if the blood flow is fast, the blood flow may appear slow on the display screen. Accordingly, in a blood vessel in which the regions where the matching degree E0 is large is dominant, the line width of the fluid information R0 to be displayed may be thickened. FIG. 15 is a diagram illustrating a display screen on which the line width of the fluid information R0 to be displayed is thickened in a blood vessel in which the regions where the matching degree E0 is large is dominant. As illustrated in FIG. 15, the line width of the fluid information R0 to be displayed in portions other than the aortic aneurysm 36 in the abdominal aorta 35 is thickened on the display screen 42.

In addition, in the above embodiment, an MM image obtained by imaging a subject by three-dimensional cine phase contrast magnetic resonance imaging is acquired as the three-dimensional image G0, and the fluid information R0 is derived by using the three-dimensional image G0. However, the present disclosure is not limited to this. A contrast CT image obtained by imaging a subject by using a contrast medium in a CT apparatus may be acquired as the three-dimensional image G0, and the analyzing unit 21 may analyze the blood flow by computational fluid dynamics (CFD), thereby deriving a flow velocity vector at each voxel position of the three-dimensional image G0 as the fluid information R0.

Furthermore, in the above embodiment, the flow velocity vector at each position in the blood vessel is derived as the fluid information R0. However, the present disclosure is not limited to this. In addition to the flow velocity vector, for example, a wall shear stress (WSS), a vorticity, or the like may also be used as the fluid information R0.

Furthermore, in the above embodiment, a blood vessel is used as a structure in which a fluid flows. However, the present disclosure is not limited to this. For example, in a case where the flow of cerebrospinal fluid is to be visualized, a ventricle of the brain in the cranium, in particular, a subarachnoid space, or a spinal subarachnoid space in a spinal canal, may also be used as the structure in which a fluid flows. In addition, a lymphatic vessel in which lymph flows may also be used.

Furthermore, in the above embodiment, an image targeting a human body is used. However, the present disclosure is not limited to this. For example, it is needless to say that the technique according to the present disclosure is applicable to a case where the flow of a fluid flowing in a pipe is analyzed.

In addition, in the above embodiment, for example, as a hardware configuration of a processing unit that executes various processes, such as the image acquiring unit 20, the analyzing unit 21, the matching degree deriving unit 22, the sampling unit 23, and the display control unit 24, any of the following various processors below can be used. The various processors include, as described above, a CPU, which is a general-purpose processor that functions as various processing units by executing software (programs), and in addition, a programmable logic device (PLD), which is a processor in which the circuit configuration is changeable after manufacture, such as an FPGA (Field Programmable Gate Array), a dedicated electric circuit, which is a processor having a circuit configuration that is specially designed to execute specific processing, such as an ASIC (Application Specific Integrated Circuit), and the like.

One processing unit may be constituted by one of these various processors or may be constituted by two or more processors of the same type or different types in combination (e.g., a combination of a plurality of FPGAs or a combination of a CPU and an FPGA). In addition, a plurality of processing units may be constituted by one processor.

As a first example for constituting a plurality of processing units by one processor, one processor may be constituted by a combination of one or more CPUs and software, and this processor may function as a plurality of processing units, as typified by a computer such as a client or a server. As a second example, a processor may be used that implements the functions of the entire system including a plurality of processing units with one IC (Integrated Circuit) chip, as typified by a system on chip (SoC) or the like. In this manner, various processing units are constituted by one or more of the above various processors in terms of hardware configuration.

More specifically, the hardware configuration of these various processors may be electric circuitry constituted by combining circuit elements such as semiconductor elements.

REFERENCE SIGNS LIST 1 fluid analysis apparatus
2 three-dimensional imaging apparatus
3 image storage server
4 network
11 CPU
12 memory
13 storage
14 communication I/F
15 display
16 input device
20 image acquiring unit
21 analyzing unit
22 matching degree deriving unit
23 sampling unit
24 display control unit
30 aortic arch
31 brachiocephalic artery
32 left common carotid artery 33 left subclavian artery
34 abdominal aorta
36 aortic aneurysm
40, 42 display screen
41 region
50 blood vessel
A1 to A4, A11 to A14 region
C0 center line
D0 cross section
LUT1 table
M magnitude data
Phx phase data
Phy phase data
Phz phase data
P0, P1-0, P2-0, P3-0 initial reference position
P1 to P8, P1-1, P1-2, P2-1, P2-2, P2-3, P3-1, P3-2, P3-3 reference position
T1 to T4 pixel-of-interest position

What is claimed is:

1. A fluid analysis apparatus comprising
at least one processor configured to:
analyze an image obtained by imaging a subject including a tubular structure in which a fluid flows, thereby deriving fluid information regarding flow of the fluid at each of pixel positions in the tubular structure;
derive, within the tubular structure included in the image, a matching degree between the fluid information at a plurality of pixel-of-interest positions set at a first sampling interval and the fluid information at a plurality of pixel positions within a predetermined region based on the pixel-of-interest positions;
set a second sampling interval for displaying the fluid information in accordance with the matching degree; and
sample the fluid information at the set second sampling interval, and cause a display to display the fluid information.

2. The fluid analysis apparatus according to claim 1, wherein the processor is configured to set the first sampling interval in accordance with a size of a region intersecting a center line of the tubular structure included in the image.

3. The fluid analysis apparatus according to claim 2, wherein the processor is configured to set the second sampling interval that is larger as the matching degree is larger.

4. The fluid analysis apparatus according to claim 3, wherein the processor is configured to set the second sampling interval to the first sampling interval if the matching degree is greater than or equal to a predetermined threshold.

5. The fluid analysis apparatus according to claim 4, wherein the processor is configured to cause the display to display representative fluid information that represents the fluid information within the region.

6. The fluid analysis apparatus according to claim 1, wherein the processor is configured to set the second sampling interval that is larger as the matching degree is larger.

7. The fluid analysis apparatus according to claim 6, wherein the processor is configured to set the second sampling interval to the first sampling interval if the matching degree is greater than or equal to a predetermined threshold.

8. The fluid analysis apparatus according to claim 7, wherein the processor is configured to cause the display to display representative fluid information that represents the fluid information within the region.

9. The fluid analysis apparatus according to claim 6, wherein the processor is configured to set the second sampling interval in accordance with a size of a region intersecting a center line of the tubular structure included in the image if the matching degree is less than a predetermined threshold.

10. The fluid analysis apparatus according to claim 9, wherein the processor is configured to set the second sampling interval in a direction intersecting the center line of the tubular structure.

11. The fluid analysis apparatus according to claim 1, wherein the processor is configured to cause the display to display the fluid information as a vector.

12. The fluid analysis apparatus according to claim 11, wherein the processor is configured to thicken a width of the vector as the second sampling interval is larger.

13. The fluid analysis apparatus according to claim 1, wherein
the image is a three-dimensional image obtained by imaging the subject by three-dimensional cine phase contrast magnetic resonance imaging, and
the processor is configured to derive, as the fluid information, a flow velocity vector of the fluid obtained by analyzing the three-dimensional image.

14. The fluid analysis apparatus according to claim 1, wherein the processor is configured to derive, as the fluid information, a flow velocity vector of the fluid obtained by simulating the flow of the fluid by an analysis using computational fluid dynamics.

15. The fluid analysis apparatus according to claim 1, wherein the tubular structure is a blood vessel, and the fluid is blood.

16. A fluid analysis method comprising:
analyzing an image obtained by imaging a subject including a tubular structure in which a fluid flows, thereby deriving fluid information regarding flow of the fluid at each of pixel positions in the tubular structure;
deriving, within the tubular structure included in the image, a matching degree between the fluid information at a plurality of pixel-of-interest positions set at a first sampling interval and the fluid information at a plurality of pixel positions within a predetermined region based on the pixel-of-interest positions; and
setting a second sampling interval for displaying the fluid information in accordance with the matching degree; and
sampling the fluid information at the set second sampling interval, and causing a display to display the fluid information.

17. A non-transitory computer readable recording medium storing a fluid analysis program for causing a computer to execute:
a procedure of analyzing an image obtained by imaging a subject including a tubular structure in which a fluid flows, thereby deriving fluid information regarding flow of the fluid at each of pixel positions in the tubular structure;
a procedure of deriving, within the tubular structure included in the image, a matching degree between the fluid information at a plurality of pixel-of-interest positions set at a first sampling interval and the fluid information at a plurality of pixel positions within a predetermined region based on the pixel-of-interest positions; and
a procedure of setting a second sampling interval for displaying the fluid information in accordance with the matching degree, sampling the fluid information at the set second sampling interval, and causing a display to display the fluid information.

\* \* \* \* \*